United States Patent [19]

Navas

[11] Patent Number: 5,375,823
[45] Date of Patent: Dec. 27, 1994

[54] APPLICATION OF AN IMPROVED DAMPER TO AN INTERVERTEBRAL STABILIZATION DEVICE

[75] Inventor: Fernand Navas, Charbonnieres les Bains, France

[73] Assignee: Societe PSI, Lyons, France

[21] Appl. No.: 73,417

[22] Filed: Jun. 9, 1993

[30] Foreign Application Priority Data

Jun. 25, 1992 [FR] France ................... 9208068

[51] Int. Cl.⁵ ............... F16F 1/36; A61B 17/58
[52] U.S. Cl. .................... 267/195; 267/153; 267/293; 606/61; 623/17
[58] Field of Search .............. 267/195, 64.15, 153, 267/183, 292, 293, 64.23, 64.26, 64.27, 139, 140; 188/279; 606/61, 57; 623/17

[56] References Cited

U.S. PATENT DOCUMENTS

| | | | |
|---|---|---|---|
| 1,780,724 | 10/1926 | Short. | |
| 2,287,608 | 6/1942 | French | 267/195 X |
| 2,987,291 | 6/1961 | Dyson | 267/153 X |
| 3,369,802 | 2/1968 | Wallace et al. | 267/195 X |
| 3,371,442 | 3/1968 | Carlson | 267/195 X |
| 3,710,458 | 1/1973 | Bornor et al. | 267/153 X |
| 3,752,462 | 8/1973 | Wight, Jr. | 267/140 |
| 3,901,495 | 8/1975 | Suzuki | 267/153 |
| 3,904,226 | 9/1975 | Smalley | 280/486 |
| 3,993,295 | 11/1976 | Suzuki et al. | 267/153 X |
| 4,200,268 | 4/1980 | Wiek | 267/63 |
| 4,445,674 | 5/1984 | Clayton, Jr. | 267/153 X |
| 4,591,030 | 5/1986 | Antkowiak | 267/153 X |

FOREIGN PATENT DOCUMENTS

| | | |
|---|---|---|
| 629690 | 7/1963 | Belgium. |
| 516567 | 12/1992 | European Pat. Off. ........ 606/61 |
| 1827221 | 3/1959 | Germany. |
| 279186 | 11/1964 | Netherlands. |
| 1227359 | 4/1968 | United Kingdom. |

Primary Examiner—Robert J. Oberleitner
Assistant Examiner—Peter M. Poon
Attorney, Agent, or Firm—Dowell & Dowell

[57] ABSTRACT

An improved damper, of the type comprising elements for progressively resisting, in exponential manner, the advance of a piston under the effect of a force of axial compression, which functions as a stop opposing any displacement of the piston beyond a predetermined value, in an intervertebral stabilization device.

12 Claims, 2 Drawing Sheets

APPLICATION OF AN IMPROVED DAMPER TO AN INTERVERTEBRAL STABILIZATION DEVICE

BACKGROUND OF THE INVENTION

1. Field of the Invention

The present invention relates to the application, in an intervertebral stabilization device, of certain dampers comprising means for progressively resisting in exponential manner the advance of a piston under the effect of a force of axial compression.

2. History of the Related Art

Such dampers are well known in the automobile domain. For example, U.S. Pat. No. 3,904,226 and NL-279 186 each describe a single- or double-effect damper which is capable of progressively resisting, in exponential manner, the advance of the piston, so that, after a certain stroke of the piston, the damper opposes any displacement of the piston beyond a determined value of the displacement.

To that end, the damper contains, between a bottom of a cylinder and a piston, an elastic body whose volume is smaller than that of a chamber determined by the position in the free state of the piston with respect to the bottom of the cylinder.

Such a damper is a so-called single-effect damper, i.e. it functions only in one direction. If a double-effect damper is desired, i.e. acting in two opposite directions, it suffices to place a second elastic body in the compartment located between the piston and a cover closing the cylinder opposite its bottom, in which the second elastic body has a volume smaller than that of the compartment.

SUMMARY OF THE INVENTION

The present invention relates to the application of a damper of the type comprising means for progressively resisting in exponential manner the advance of a piston under the effect of a force of axial compression, the means constituting a stop opposing any displacement of the piston beyond a determined value of the displacement, to an intervertebral stabilization device.

The damper includes other means for progressively resisting in exponential manner the recoil of the piston under the effect of a force of extension of direction opposite that of compression.

The means for resisting any progressive displacement of the piston consists in at least one elastic body whose volume is smaller than that of a chamber of a cylinder in which it is contained.

Variation in the volume of the chamber or the compartment thus brings about a deformation of the corresponding elastic body which is opposed by the non-deformability of the chamber wall, with the result that a force progressively opposes the displacement of the piston until it is stopped when the force becomes exponential.

BRIEF DESCRIPTION OF THE DRAWINGS

The invention will be more readily understood on reading the following description with reference to the accompanying drawings, in which.

DETAILED DESCRIPTION OF THE DRAWINGS

Figure 1:
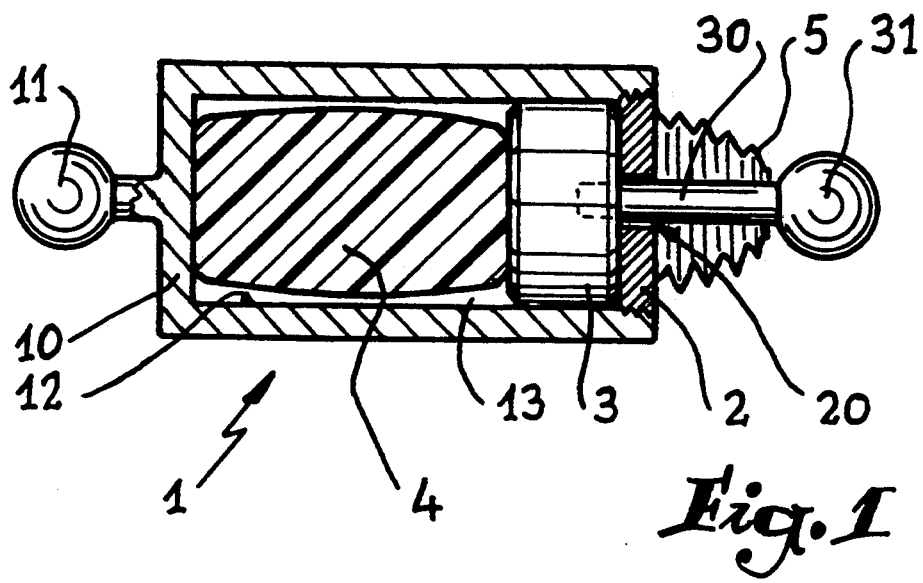
FIG. 1 is a longitudinal section through a damper according to the invention, provided to be of single-effect.

Referring now to the drawings, FIG. 1 shows a damper according to the invention essentially comprising a cylinder 1 of which the outer face of the bottom 10 is secured to a ball joint 11, this cylinder being closed at its end opposite the bottom 10 by a cover 2. Before this cover is mounted, there is engaged inside the cylinder 1 a piston 3 mounted a rod 30 with a ball joint 31, the rod 30 traversing a central hole 20 in the cover 2. It will be observed that the height of the piston 3 is large with respect to the length of the cylinder 1, so as to ensure good guiding of the piston in the bore 12 of said cylinder when the piston moves in the bore.

Prior to introducing the piston 3 in the bore 12 of the cylinder 1, there is placed against the inner face of the bottom 10 an elastic body 4 such as a block of natural or synthetic rubber whose volume in the free state is slightly smaller than that of the chamber 13, determined by the inner volume of the cylinder 1 defined between its bottom 10 and the piston 3 when the piston rests against the cover 3. A bellows element 5, secured to cover 2 and rod 30, provides a seal at the passage of the rod in the hole 20 in the cover.

When a force acts on the ball joints 11 and 31 in the direction of each other (compression), it provokes a translation of the piston 3 from its rest position in which it abuts against the inner face of the cover 2 in the direction of the bottom 10 of the cylinder 1. Such displacement causes a deformation of the elastic body 4, which is countered by the rigidity of the walls of the cylinder 1, with the result that the body 4 opposes the displacement of the piston 3 with an increasing resistance. When the volume of the chamber 12 is equal to that of the elastic body 4 already compressed, the resistance developed by the body against the displacement of the piston 3 becomes exponential and, at the limit, acts as a stop preventing any subsequent displacement of the piston 3, so that, in fact, the displacement of the piston is thus stopped. Of course, the damper shown in FIG. 1 functions only in the direction of compression, i.e. when a force is applied to bring ball joints 11 and 31 closer.

Figure 2:
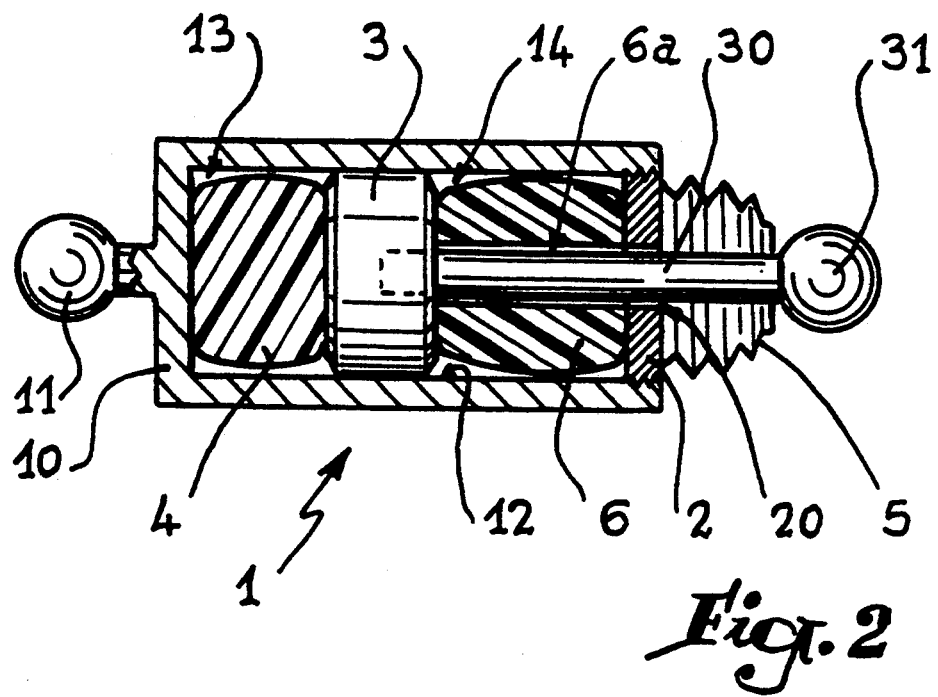
FIG. 2 is a view similar to that of FIG. 1, but illustrating a double-effect damper.

In the embodiment of FIG. 2, in the free state, piston 2 is not in abutment against cover 3, but it forms therewith a compartment 14 in which is placed an elastic block 6 comprising a central hole 6a which is traversed by rod 30 of piston 3. There again, the volume of the second elastic body 6 is slightly smaller, in the free state, than that of compartment 14.

Functioning of the embodiment of FIG. 2 is strictly the same as that of the damper illustrated in FIG. 1 when it resists a force of compression tending to bring ball joints 11 and 31 closer. In identical manner, when a force of extension is applied to the damper of FIG. 2, i. e. when this effort tends to move ball joints 11 and 31 apart, the piston compresses the elastic body 6 which resists its displacement more and more as the volume of the elastic body 6 approaches that of compartment 14. The resistance then becomes exponential. It forms, when the second elastic body 6 becomes incompressible, a stop which limits any subsequent displacement of piston 3.

Figure 3:
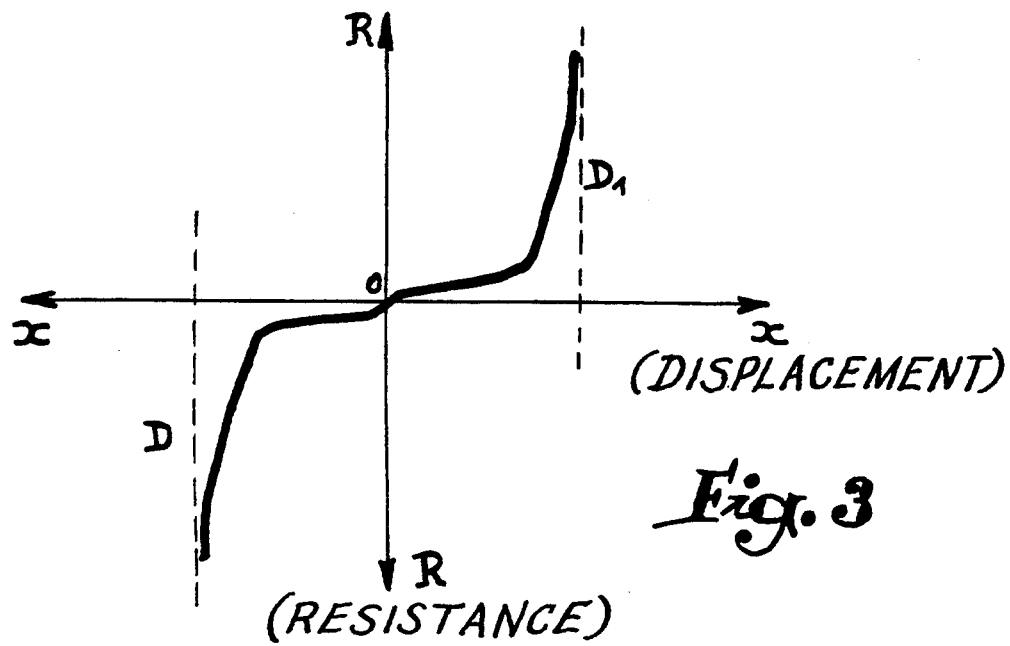
FIG. 3 is a curve illustrating the variations in the force developed by the damper of FIGS. 1 and 2.

FIG. 3 shows the curve which illustrates the variation in the resistant force of the damper of FIG. 2. The left-hand part of the curve corresponds to an effort of compression applied on the damper and which represents in fact a negative displacement illustrated from the origin. The resistance R increases for the majority of the displacement relatively slightly with respect to this displacement, then becomes exponential, finishing asymptotic at a straight line D parallel to the Y-axis R.

If, on the contrary, the displacement of the damper is positive (case of a traction), the curve illustrating the resistance of the damper is virtually symmetrical with respect to that corresponding to a compression, this part of the curve becoming asymptotic at a straight line D1 likewise parallel to the Y-axis R.

Of course, the curve is symmetrical if the two elastic bodies 4 and 6 present the same characteristics of volume and flexibility and if chamber 13 and compartment 14 are of the same volume. On the contrary, both the characteristics of the elastic bodies 4 and 6 and the volumes of chamber 13 and of compartment 14 may be varied so as to obtain different resistant efforts upon compression or upon traction.

Figure 4:
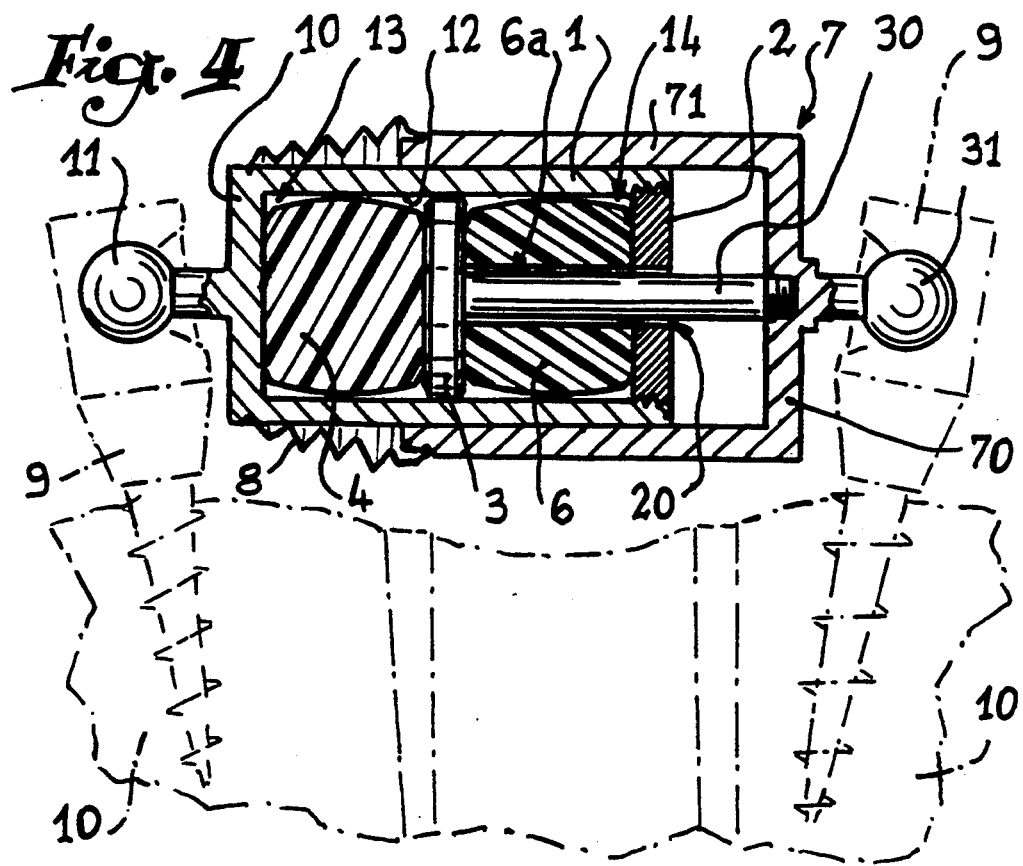
FIG. 4 is a variant embodiment of the device of FIG. 2, showing, in broken lines, the elements enabling it to be associated with two vertebrae.

Finally, FIG. 4 presents another embodiment of the damper of FIG. 2. It is observed in this Figure, and in FIG. 1, that the piston 3 presents a considerable width in order to ensure guiding thereof in the bore of the cylinder 1. FIG. 4 shows another way of ensuring the guiding in question. In this embodiment, the piston 3 is of small thickness, while its rod 30 is secured to a tubular cage 7 via its bottom 70, the skirt 71 of this cage sliding closely with respect to the outside of the cylinder 1. A bellows element 8 similar to 5 connects the cylinder 1 and the bottom of the skirt 71 of the cage 7 to ensure tightness thereof.

FIG. 4 illustrates two implants 9 whose head is mounted to pivot with respect to ball joints 11 and 31, while their body is screwed in two vertebrae 9 so as to constitute an intervertebral stabilization device functioning in parallel and in the same manner as the disc separating the two vertebrae.

In fact, the device according to the invention is not intended to replace the intervertebral disc. The device is provided to relieve the disc when it withstands forces of compression and of traction.

Of course, it may be provided that piston 3 is never totally free and always maintained stable by the existence of spontaneous, opposite forces developed by the two elastic bodies 4 and 6. These forces not being zero at the point of equilibrium, an elastic stabilization is thus obtained of piston 3 at a point of equilibrium, so that any displacement in traction or in compression exerted on the damper immediately brings about an opposing reaction. This initial pre-stress may, of course, be fixed by varying the volume and the characteristics of the elastic bodies in a damper of which the volume of the chamber and compartment remains constant.

As indicated hereinabove, a particularly advantageous application of the damper according to the invention consists in the creation of an intervertebral stabilization device, although other different medical applications may be envisaged for example in combination with any prosthesis system, the damper being used in the form of embodiment of FIG. 1 (single-effect) or FIGS. 2 and 4 (double-effect).

It must, moreover, be understood that the foregoing description has been given only by way of example and that it in no way limits the domain of the invention which would not be exceeded by replacing the details of execution described by any other equivalents. In particular, it may be provided to place a dish-shaped element between each elastic body 4, 6 and to place between each dish element and the bottom of the cylinder or cover, respectively, a spring (not shown) increasing the reaction developed by the damper to compression or extension or under both stresses.

What is claimed is:

1. An intervertebral stabilization device for attachment into two vertebrae comprising, a housing having opposite ends and defining an internal chamber, one of said ends of said housing being closed, a piston means slidably deposed within said internal chamber, a first rod element extending outwardly relative to said chamber from said one end of said housing and a second rod element extending outwardly relative to said chamber from said piston means, each of said first and second rod elements having outer ends, a first ball joint on said outer end of said first rod element and a second ball joint on said outer end of said second rod element for attachment into two vertebrae, a first elastic body damper means disposed within said chamber, said first elastic body damper means being engagable by said piston means so as to resist compression of said first elastic body damper means by said piston means under the effect of a force urging said piston means in axial compression relative to said elastic body dampen means, and said first elastic body damper means functioning as a stop to prevent further displacement of said piston means under the force of axial compression after a predetermined displacement of said piston means.

2. The intervertebral stabilization device of claim 1 including a cover means mounted to said other end of said housing, an opening through said cover means, and said second rod element extending through said opening in said cover means.

3. The intervertebral stabilization device of claim 2 including a bellows means mounted in surrounding relationship with respect to said second rod element and having a first portion engaging said cover means and a second portion adjacent said second ball joint whereby said bellow means substantially seals said opening in said cover means.

4. The intervertebral stabilization device of claim 3 including a second elastic body damper means mounted within said chamber between said piston means and said cover means, and an opening in said second elastic body damper means through which said second rod element extends whereby said second elastic body damper means opposes movement of said piston by application of a force in axial extension relative to said piston means.

5. The intervertebral stabilization device of claim 4 in which said housing is generally cylindrical and having inner wall portions, said piston means being of a size to slidably engage said inner wall portions, and said first and second elastic body damper means being of a size to be expandable radially outwardly towards said inner wall portions upon the application of forces in compression and extension, respectively.

6. The intervertebral stabilization device of claim 5 including a pair of anchor means, each of said anchor means having socket means for receiving one of said first and second ball joints whereby said ball joints may be pivotable relative to said anchor means.

7. The intervertebral stabilization device of claim 1 in which said housing includes inner wall portions, said piston means having an outer secondary housing of a size to be slidably engagable with said inner wall portions of said housing and defining a secondary internal chamber, said secondary housing having a closed end and on opposite end, said second rod element extending from said closed end of said secondary housing, said first elastic body damper means being disposed within said secondary internal chamber, said piston means including a head portion mounted within said secondary chamber in opposing relationship with said closed end wall of said secondary housing, a rod mounted to said head portion and extending outwardly therefrom and into engagement with said closed one end of said housing.

8. The intervertebral stabilization device of claim 7 in which said head portion of said piston means divides said secondary internal chamber into first and second compartment, said first elastic body damper means being disposed within said first compartment so as to be intermediate said closed end of said secondary housing and said head portion and a second elastic body damper means mounted within said second compartment of said secondary internal chamber, a cover means for closing said opposite end of said secondary housing, and an opening in said cover means and an opening through said second elastic body damper means through which said rod extends.

9. The intervertebral stabilization device of claim 8 including a bellows means encircling said secondary housing and having one end secured to the other of said ends of said housing and a second end secured to said secondary housing adjacent said closed end thereof.

10. The intervertebral stabilization device of claim 8 in which said secondary housing is generally cylindrical and having inner wall portions, said head portion of said piston means being of a size to slidably engage said inner wall portions, and said first and second elastic body clamper means being of a size to be expandable radially outwardly towards said inner wall portions upon the application of forces in compression and extension, respectively.

11. The intervertebral stabilization device of claim 10 including a pair of anchor means, each of said anchor means having socket means for receiving one of said first and second ball joints whereby said ball joints may be pivotable relative to said anchor means.

12. An intervertebral stabilization device for attachment into two vertebrae comprising, a housing having opposite ends and defining an internal chamber, one of said ends of said housing being closed, a piston means slidably deposed within said internal chamber, a first rod element extending outwardly relative to said chamber from said one end of said housing and a second rod element extending outwardly relative to said chamber from said piston means, each of said first and second rod elements having outer ends for attachment into two vertebrae, a first elastic body damper means disposed within said chamber, said first elastic body damper means being engagable by said piston means so as to resist compression of said first elastic body damper means by said piston means under the effect of a force urging said piston means in axial compression relative to said elastic body dampen means, and said first elastic body damper means functioning as a stop to prevent further displacement of said piston means under the force of axial compression after a predetermined displacement of said piston means, a cover means mounted to said other end of said housing, an opening through said cover means, and said second rod element extending through said opening in said cover means, and a bellows means mounted in surrounding relationship with respect to said second rod element and having a first portion engaging said cover means and a second portion adjacent said outer end of said second rod element whereby said bellow means substantially seals said opening in said cover means.

* * * * *